United States Patent
Klein et al.

(10) Patent No.: US 7,117,741 B2
(45) Date of Patent: Oct. 10, 2006

(54) METHOD AND DEVICE FOR ULTRASONIC VIBRATION DETECTION DURING HIGH-PERFORMANCE MACHINING

(75) Inventors: Marvin Klein, Pacific Palisades, CA (US); Bruno Pouet, Los Angeles, CA (US); Jerome Eichenberger, Los Angeles, CA (US)

(73) Assignee: Lasson Technologies, Inc.

( * ) Notice: Subject to any disclaimer, the term of this patent is extended or adjusted under 35 U.S.C. 154(b) by 158 days.

(21) Appl. No.: 10/807,754

(22) Filed: Mar. 23, 2004

(65) Prior Publication Data

US 2005/0210983 A1   Sep. 29, 2005

(51) Int. Cl.
  *G01N 29/12* (2006.01)
  *G01N 29/28* (2006.01)
  *G01N 29/44* (2006.01)
(52) U.S. Cl. .......................... 73/579; 73/644
(58) Field of Classification Search ............ 73/579, 73/644
See application file for complete search history.

(56) References Cited

U.S. PATENT DOCUMENTS

| | | | | |
|---|---|---|---|---|
| 2,751,783 A | * | 6/1956 | Erdman | 73/634 |
| 3,585,577 A | * | 6/1971 | Rollwitz et al. | 367/90 |
| 4,507,969 A | * | 4/1985 | Djordjevic et al. | 73/644 |
| 4,738,139 A | * | 4/1988 | Blessing et al. | 73/644 |
| 5,001,932 A | * | 3/1991 | Light et al. | 73/644 |
| 5,076,102 A | * | 12/1991 | Sato et al. | 73/587 |
| 5,086,775 A | * | 2/1992 | Parker et al. | 600/453 |
| 6,068,597 A | * | 5/2000 | Lin | 600/443 |

* cited by examiner

*Primary Examiner*—Hezron Williams
*Assistant Examiner*—Rose M. Miller
(74) *Attorney, Agent, or Firm*—D. Morgan Tench (57) ABSTRACT

Dynamic vibration monitoring of a cutting tool or workpiece is provided by propagating an ultrasonic carrier beam in a stream of fluid flowing from a probe chamber, which includes a transducer, to the cutting tool or workpiece target area. The modulated ultrasonic beam reflected from the target is detected via a transducer in the chamber, and is demodulated to provide measurements of vibrational surface displacement and velocity. The method is insensitive to the target surface roughness and can be used for dynamic characterization prior to machining, and for monitoring during the machining operation. The device is inexpensive and robust to the machining environment, and can be applied to small cutting tools.

18 Claims, 11 Drawing Sheets

METHOD AND DEVICE FOR ULTRASONIC VIBRATION DETECTION DURING HIGH-PERFORMANCE MACHINING

U.S. GOVERNMENT RIGHTS

This invention was made with Government support under Grant No. DMI-9960737 awarded by the National Science Foundation and Contract Nos. DASG60-02-P-0059 and DASG60-03-C-0072 awarded by the Missile Defense Agency. The Government has certain rights in this invention.

BACKGROUND OF THE INVENTION

1. Field of the Invention

The present invention is generally related to vibration monitoring and is more specifically concerned with vibration monitoring of cutting tools used for high-performance machining.

2. Description of the Related Art

Driven by cost reduction, high productivity, throughput and quality goals, the machining industry has an increasing need for improved characterization of cutting tools and for controlling vibration and chatter during the machining process. If uncontrolled, vibration and chatter can reduce surface finish quality, limit dimensional accuracy, increase tool wear and create high levels of noise. These undesirable performance attributes can, in turn, lead to increased machine wear, reduced throughput and higher scrap rates. Furthermore, there are growing demands for high-speed milling, for the use of small tools, and for machining advanced materials with poor machining characteristics, all of which exacerbate vibrational problems. Conventional approaches for control of vibration and chatter, such as increasing the stiffness of the tool and reducing the cutting depth or machine speed, clearly reduce production throughput and are no longer satisfactory.

Recently, more sophisticated approaches that take advantage of modern dynamic models and improved sensors and controls have been developed. These approaches typically utilize knowledge of the mass, stiffness, and vibrational and damping characteristics of the tool to estimate the cutting depth limits and the optimal spindle speed. Only limited control has been attained since prior art sensors permit dynamic characterization of the tool only prior to the machining operation. Optimal control requires that vibration be sensed as close as possible to the tool tip during the actual machining process since tool vibration and chatter are significantly affected by interaction between the tool and the workpiece.

One prior art method for predicting vibrational characteristics of a cutting tool involves exciting the static tool with an impulse hammer and detecting the resulting vibrations via an accelerometer mounted at or near the tip of the tool. The force of the impulse hammer excitation is usually chosen to simulate the force expected during the cutting process, which typically ranges from tens of Newtons for small tools up to a few thousand Newtons for larger tools. Nonetheless, the impulse hammer method does not adequately predict vibration during the machining process since accelerometers cannot be used to detect vibration of a rotating tool. A further limitation of the impulse hammer method is that accelerometers are typically too large and/or too heavy for use with the small tools often employed by mold manufacturers and the rapid prototype industry, for which the tool diameter may be as small as $1/64^{th}$ inch. Strain gages have been adapted for sensing vibration but must also be mounted on the tool and cannot be used during tool rotation.

For dynamic vibrational characterization of a rotating tool, a non-contact sensor is required. Prior art methods for detecting cutting tool vibrations have employed a number of non-contact sensors, including capacitive probes, inductive probes, laser Doppler vibrometers, and acoustic pickup devices (e.g., microphones). An alternative prior art method involves detection of tool vibration from an indirect measurement, via measured fluctuations in tool rotation speed or spindle power requirements, for example.

There is no commercially available vibration sensor that provides the capabilities needed for advanced machining. These capabilities include dynamic tool vibration monitoring before and during the machining process, high measurement sensitivity and accuracy, insensitivity to the machining environment, minimal mechanical loading, compactness and low-cost. It would also be very beneficial to be able to monitor vibration of the workpiece, which may be appreciable for advanced materials that are difficult to machine. The availability of an accurate, robust and low-cost sensor to measure tool vibrational characteristics would be of great practical value.

In principle, a laser beam could be used to remotely detect vibration of a rotating tool via measurements of displacement of the tool surface as a function of time. However, such measurements are strongly influenced by the surface roughness of the tool, which greatly limits the utility of the method. Ultrasonic reflection measurements are much less sensitive to surface roughness of the target and have been shown to be useful for detecting vibration of static parts immersed in a liquid in a tank [D. Royer and O. Casula, Appl. Phys. Lett. 67(22), 27 (1995)]. It is not obvious how this approach could be applied to dynamic vibration monitoring of real-world cutting tools. Ultrasonic vibration measurements made in air are much less sensitive (compared to liquid phase measurements) due to scattering effects, and are significantly affected by turbulent flow of the hot air typically produced by friction during machining operations, as well as by mist and dust that are frequently present in the environment.

SUMMARY OF THE INVENTION

The present invention provides a method and a device for ultrasonically detecting vibration of a target, which may be a predetermined area of a rotating cutting tool, before or during a machining operation. The method and the device may also be used to detect vibration of a workpiece at various locations, including areas close to the cutting zone. The invention provides high measurement sensitivity and accuracy, and the device is compact, low-cost, and robust with respect to the machining environment.

In the method of the present invention, a stream of a fluid is caused to flow from a chamber to a target under interrogation, which preferably includes at least a portion of a rotating tool or a workpiece. An ultrasonic carrier beam of a predetermined frequency, preferably in the range from 100 kHz to 10 MHz, is provided in the fluid by a first transducer in contact with the fluid in the chamber, and is propagated along the fluid stream to the target. The first transducer is driven by an electrical signal, of the predetermined frequency, provided by an electrical driver. Reflection of the ultrasonic carrier beam from the target generates a reflected ultrasonic beam that is modulated by target vibration. The reflected ultrasonic beam is propagated back along the fluid stream to the chamber, and is converted to a return electrical signal by the first transducer or a second transducer in contact with the fluid in the chamber. The return electrical signal, which incorporates modulation of the ultrasonic carrier beam by target vibration, is processed by a demodulator to provide a measure of a vibrational characteristic of the target. The demodulator is preferably a phase demodulator. If the first transducer is also used to detect the return ultrasonic beam, a directional coupler is disposed between the driver and the transducer so as to direct the return electrical signal to the demodulator.

The stream of fluid serves as a low-loss medium for propagating ultrasonic waves to and from a desired area of interrogation on the tool or workpiece. If the fluid stream length exceeds a few wavelengths of the ultrasonic beam, and the fluid stream diameter is on the order of the ultrasonic wavelength, then the fluid stream acts as a waveguide for the ultrasonic beam. The use of a fluid stream permits the ultrasonic beam to be propagated with low loss over long distances. A free-standing (unconfined) fluid stream of about 3/16 inch in diameter has been found to serve as an effective waveguide for a 1-MHz ultrasonic beam.

The stream of fluid is produced by causing fluid to flow through an outlet in the chamber. The outlet is preferably circular and sized to provide a fluid stream of the desired diameter. Fluid is fed to the chamber from a fluid source. Fluid may be caused to flow by a mechanical pump, hydraulic pressure, gas pressure, gravity feed, or any other suitable means. A preferred means of producing fluid flow is a mechanical pump. The fluid is preferably a cutting fluid, or a fluid that is compatible with a cutting fluid. The viscosity of the fluid used for measurements according to the present invention may be within the viscosity range of typical cutting fluids (1 to 18 centipoises).

The fluid stream may be free standing over at least a portion of its length. The use of a free-standing fluid stream enables the ultrasonic beam to be accurately directed onto otherwise inaccessible areas of the tool or workpiece. The fluid stream may also be confined within a tube over at least a portion of its length. Such a confinement tube may be flexible or rigid, straight or curved, and the chamber outlet and the tube may be circular or may have another cross-sectional geometry. The fluid and the surrounding confinement tube form a composite waveguide. The cross-section of the chamber outlet and/or the confinement tube may be selected to provide laminar flow, or a fluid stream of a desired shape. Turbulence in the fluid stream should be avoided so as to minimize interference from extraneous scattering or reflection of the ultrasonic beams. A confinement tube enables use of low fluid flow rates to avoid fluid turbulence. A baffle may be disposed within the chamber to provide laminar flow of the fluid within the chamber and the fluid stream. A protective tube having an inside diameter larger than the diameter of the free-standing fluid stream may be used to protect the fluid stream from machining debris and cutting fluid spray.

The ultrasonic carrier beam of the present invention preferably comprises a substantially continuous ultrasonic wave, for which demodulation is facilitated. An ultrasonic beam pulsed at a high repetition rate could also be used but, in this case, it would be more difficult to extract the vibrational characteristic of the target from the reflected ultrasonic beam.

Pulsed ultrasonic waves have been used in the prior art to detect flaws in structural materials. Such prior art ultrasonic inspection methods involve propagation of ultrasonic waves within stationary solid materials and are not suitable for vibration monitoring. The use of a fluid stream to propagate and direct ultrasonic waves according to the present invention provides high sensitivity to localized vibrations, which is not attainable with prior art methods.

Vibrational characteristics of the target provided by demodulation of the reflected ultrasonic beam according to the present invention include the displacement of the vibrating surface. The well-known Doppler effect produces phase modulation of the reflected wave in proportion to the surface displacement. Additional phase modulation is produced in proportion to the surface velocity of the vibrating target and also depends on the length of the fluid stream. The output signal corresponding to the surface velocity component can be significantly increased by increasing the length of the fluid stream. A similar signal enhancement can be obtained by introducing an electrical time delay into the signal path via analog electronic means or via a separate ultrasonic delay line. A preferred electronic approach is a lumped element delay line. A preferred ultrasonic approach is a bulk compressional wave delay line in water or another fluid with a low sound velocity to provide increased temporal delay.

The method of the present invention may further include measuring vibration of a transducer used to detect vibration of a tool or a workpiece, and canceling noise signals produced by the transducer vibration from the transducer return electrical signal. Transducer vibration resulting from the machining operation under interrogation or from other sources may be detected, for example, via an accelerometer mounted on the transducer or the chamber. Canceling the effects of transducer vibration on the transducer return signal may improve the accuracy and precision of vibration measurements according to the present invention.

An ultrasonic fluid probe device for vibration monitoring according to the present invention generally comprises: a chamber containing a fluid and having an outlet through which a stream of fluid is caused to flow from the chamber to a target to be interrogated; a fluid source; a means for causing fluid to flow; a first transducer in contact with the fluid in the chamber and coupled to an electrical driver for generating an ultrasonic carrier beam of a predetermined ultrasonic frequency; a second transducer in contact with the fluid in the chamber for receiving a reflected ultrasonic beam that is modulated by vibration of the target and for generating a return electrical signal; and a demodulator, preferably a phase demodulator, for processing the return electrical signal to provide a measure of a vibrational characteristic of the target. A preferred phase demodulator provides an electrical signal proportional to the target vibrational displacement. An electrical signal proportional to the target vibrational surface velocity may also be present under certain conditions.

Suitable means for causing fluid flow include a mechanical pump, a hydraulic pressure system, a pressurized gas, and gravity, coupled with appropriate plumbing. The outlet in the chamber through which a steam of the fluid is caused to flow is preferably circular but may have another cross-sectional geometry. The size and shape of the outlet are preferably chosen to provide laminar flow and a fluid stream that serves as an effective waveguide for the ultrasonic carrier beam over a predetermined distance between the chamber and the target.

The device of the present invention may further comprise a baffle positioned in the chamber so as to provide laminar flow of the fluid in the chamber and the fluid stream. Appropriate baffling systems will be apparent to those skilled in the art.

The first transducer may also receive the reflected ultrasonic wave so that the device does not include a second transducer. In this case, the device further comprises a directional coupler, disposed between the driver and the transducer, to direct the return electrical signal to the demodulator. Transducers are preferably mounted to the chamber. When two transducers are employed, they are preferably positioned coaxially or side-by-side.

The device of the present invention may further comprise a tube, attached to the chamber around the chamber outlet, for confining at least a portion of the stream of fluid that flows from the chamber to the target. Such a fluid confinement tube allows the integrity of the fluid stream to be maintained over a much longer distance compared to an unconfined stream. A confinement tube thus enables access to areas not accessible with an unconfined fluid stream. A fluid confinement tube also serves to protect the fluid stream from machining debris and cutting fluid spray. In addition, a fluid confinement tube permits use of a longer fluid stream to enhance the strength of the ultrasonic phase modulation signal. This signal is associated with the surface velocity of the vibrating target and increases with increased length of the fluid stream. A fluid confinement tube should not be so long that ultrasonic propagation losses are too large.

The device of the present invention may further comprise a protective tube for protecting at least a portion of a free-standing fluid stream from machining debris and cutting fluid spray. Such a protective tube has an inside diameter that is larger than the diameter of the fluid stream and is substantially coaxial with the free-standing fluid stream. The protective tube may be mounted to the chamber around the chamber outlet, or may be mounted to a fluid confinement tube.

The device of the present invention further comprises a fluid source in fluid communication with the chamber and the fluid stream. Preferably, fluid is caused to flow from the fluid source to the chamber so that laminar flow is maintained within the waveguide comprising the fluid stream and at least a portion of the fluid within the chamber. The fluid flow system should be designed so as to avoid introducing air bubbles in the chamber, which may interfere with propagation of the ultrasonic beams.

The device of the present invention may further comprise a contact vibrometer (a contact accelerometer, for example) disposed on a component of the ultrasonic fluid probe (the chamber or a transducer, for example). In this case, vibration signals from the contact vibrometer can be used to cancel transducer vibration noise signals that would otherwise interfere with the tool vibration measurement.

A main feature of the present invention is the use of a fluid stream as a low-loss medium for propagating ultrasonic waves between a transducer and a vibrating target to be interrogated. The fluid stream can be directed selectively to a desired area of interrogation on the tool or workpiece, including poorly accessible areas. The invention enables dynamic vibration measurements of a cutting tool or a workpiece, before and during machining.

The present invention finds application across all military and commercial sectors with critical machining requirements. Most notably, the invention can be used to increase productivity and reduce unit cost in the production of structural components, active components (such as turbine blades) and precision components, as well as molds and dies. Both the military and commercial sectors are now focusing their manufacturing efforts on design for reproducibility, high quality and lower cost. The present invention will facilitate all of these goals.

Further features and advantages of the invention will be apparent to those skilled in the art from the following detailed description, taken together with the accompanying drawings.

DETAILED DESCRIPTION OF THE INVENTION

Ultrasonic Fluid Probe System

Figure 1:
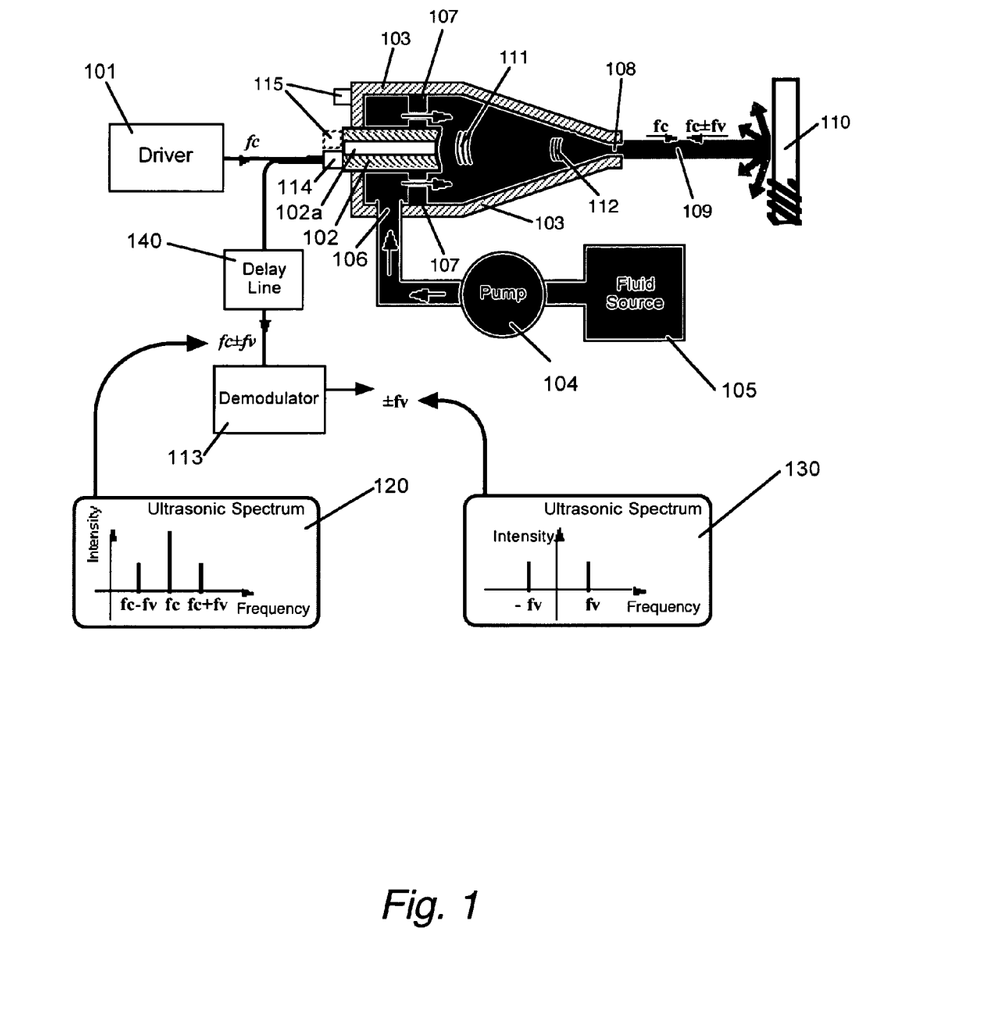
FIG. 1 is a block diagram illustrating the basic operation of an ultrasonic fluid probe system employing a free-standing fluid stream as a waveguide in accordance with the present invention.

FIG. 1 illustrates the basic operation of a preferred ultrasonic fluid probe system of the present invention employing a single transducer and a free-standing fluid stream as an ultrasonic waveguide. Driver 101 provides an electrical signal of carrier frequency $f_c$ to transducer 102, which is mounted through a wall of chamber 103. As indicated by the arrows in FIG. 1, pump 104 causes a fluid to flow from fluid source 105 into chamber 103 via inlet 106, past baffle 107, and through outlet 108 in chamber 103 to produce fluid stream 109 that impinges target 110, which is depicted as a cutting tool but may also be a workpiece. Ultrasonic carrier beam 111 produced by transducer 102 is propagated along fluid stream 109 to target 110. Return ultrasonic beam 112 reflected from target 110 and modulated by vibration frequency $f_v$ of target 110 is guided back to transducer 102 via fluid stream 109. Transducer 102 converts return ultrasonic beam 112 into return electrical signal $f_c \pm f_v$, which is directed to demodulator 113 by directional coupler 114. Typically, demodulator 113 is a phase demodulator, which converts ultrasonic spectrum 120 to ultrasonic spectrum 130. The output signal corresponding to the surface velocity component can be significantly increased by increasing the length of fluid stream 109. A similar signal enhancement can be obtained by introducing an electrical time delay into the signal path via analog electronic means or via a separate ultrasonic delay line 140. Chamber 103 is preferably shaped so as to provide laminar fluid flow within fluid stream 109. Suitable results are provided by a cylindrical chamber with one end tapered in a cone to the diameter of the fluid stream. The cross-sectional area of inlet 106 should be larger than that of outlet 108. An accelerometer 115 mounted on chamber 103 or on transducer 102 (indicated by box with dashed sides) may be included in the device to permit the effects of transducer vibration to be taken into account so as to improve the accuracy and precision of vibration measurements according to the present invention. Typically, the measured acceleration is integrated twice to obtain a displacement signal, which is used to correct the signal from the ultrasonic probe for vibration of the transducer.

As also shown in FIG. 1, a second transducer 102a may be used to detect return ultrasonic beam 112. In this case, directional coupler 114 is not needed. Second transducer 102a is preferably placed side-by-side or coaxially (as shown) with transducer 102.

Operation of the ultrasonic fluid sensor of FIG. 1 involves directing fluid stream 109 at target 110, which may be a cutting tool or a workpiece being machined. Ultrasonic carrier beam 111 is propagated in fluid stream 109 and reflected ultrasonic beam 112, modulated by the vibrating surface of target 110, is propagated back along fluid stream 109 to transducer 102. When target 110 is not vibrating, reflected ultrasonic beam 112 has the same frequency spectrum as ultrasonic carrier beam 111. When target 110 is vibrating, the frequency spectrum of the reflected ultrasonic beam has added sidebands according to the Doppler effect. The target vibrational characteristics are determined simply by comparing the frequency spectrum of the ultrasonic carrier beam 111 with that of the reflected ultrasonic beam 112.

The active ultrasonic fluid probe system of FIG. 1 has a number of features that make it particularly attractive for vibration measurements on cutting tools:

1. Because ultrasonic wavelengths fall in the millimeter range, the ultrasonic fluid probe of the present invention exhibits high sensitivity to target vibration and low sensitivity to the target surface finish. Polishing of the target surface is not required, which is not the case for analogous optical techniques.

2. The fluid used for the vibration measurement can also be used for cooling and/or lubrication.

3. The ultrasonic fluid probe is very sensitive to target vibration. Nanometer displacement sensitivity has been measured for the ultrasonic fluid probe.

4. The ultrasonic fluid probe can be scaled down to accommodate small tool sizes, which is not the case for contact sensors, such as accelerometers.

5. Due to the non-contact nature of the ultrasonic fluid probe, measurements on the cutting tool during the machining operation are possible.

6. The same ultrasonic fluid probe can be used for both dynamic on-machine characterization prior to machining and for monitoring during the machining process.

7. The low cost, compact size and rugged construction of the ultrasonic fluid probe allows economical, on-machine, multi-station monitoring.

The method of the present invention offers significant advantages compared to similar methods based on the laser Doppler vibrometer:

Speckle noise, which is a well-known problem for detection techniques based on coherent laser light, does not significantly affect the ultrasonic measurements of the present invention. Speckle is manifested as random spatial distributions of phase and intensity for laser light reflected from an optically rough surface, such as that of a cutting tool. Target translation or rotation causes spatial and temporal changes in the speckle pattern, generating "speckle noise" that directly affects the laser vibrometer output signal. Since ultrasonic wavelengths are about 3 orders of magnitude larger than typical laser optical wavelengths, ultrasonic measurements are not affected by speckle noise. A surface that is rough compared to an optical wavelength is generally smooth relative to ultrasound wavelengths. The active ultrasonic fluid probe of the present invention can thus be used on "as-machined" surfaces without loss of sensitivity.

The ultrasonic fluid probe of the present invention exhibits high sensitivity, comparable to that of the laser Doppler vibrometer, despite the relatively large ultrasonic wavelength. This is due in part to the different noise sources for ultrasonic and optical measurements. For piezoelectric transducers used for ultrasonic signal detection, the response is linear so that the detection sensitivity is limited only by thermal noise. In this case, the noise increases linearly with increasing signal strength. By contrast, an optical probe is limited by shot noise due to the quadratic behavior of the photodetector and thus the signal-to-noise ratio increases with the square root of the detected signal intensity. A prototype ultrasonic fluid probe according to the present invention exhibited an optimum sensitivity of $0.9 \text{ nm}/(\text{Hz})^{1/2}$ (at a very low fluid flow rate).

Piezoelectric transducers are robust and low cost compared to laser Doppler vibrometers.

Demodulation Methods

Figure 2:
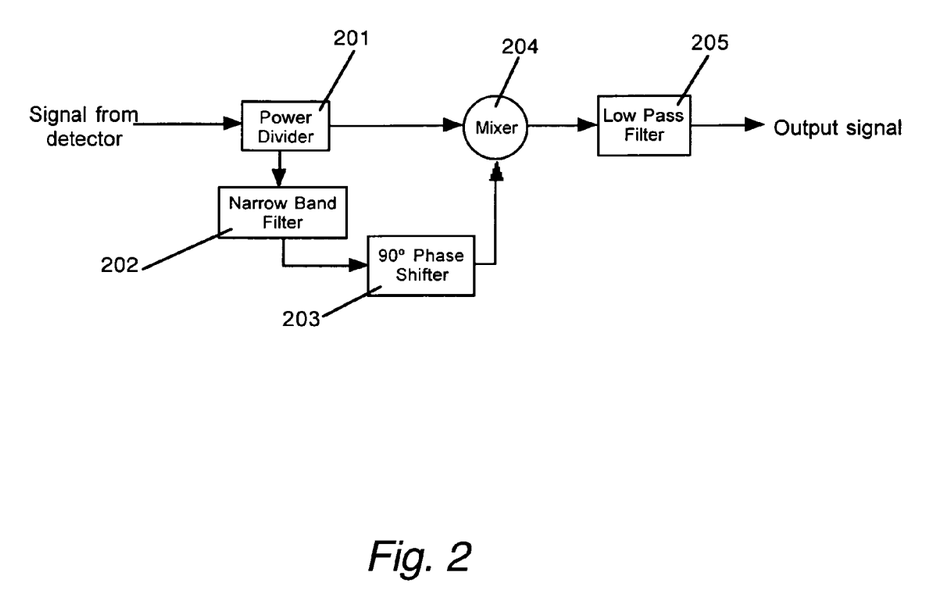
FIG. 2 is a block diagram of a coherent phase demodulator incorporating a narrowband filter.
Figure 3:
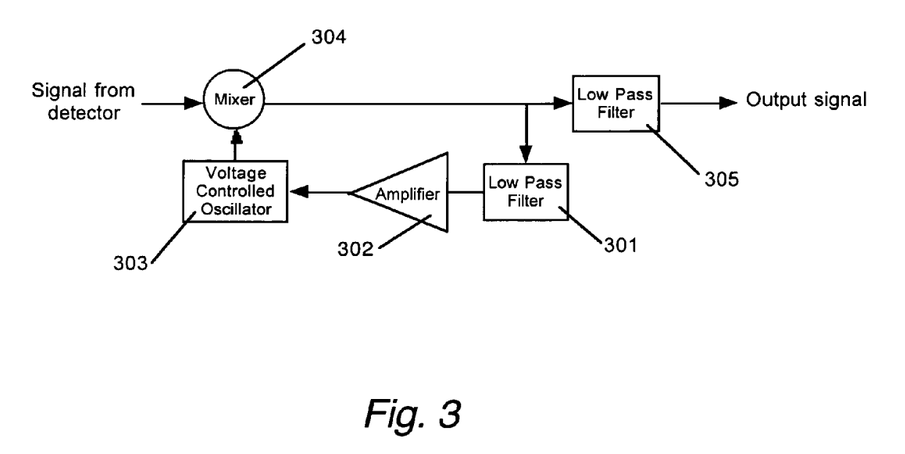
FIG. 3 is a block diagram of a coherent phase demodulator utilizing a voltage controlled oscillator (VCO).

Depending on the amplitude and frequency content of the target motion, various demodulation techniques can be used. For high-performance machining applications, the vibration frequency of interest is between 20 Hz and 30 kHz. The vibration displacement amplitude of interest is in the micrometer range and, in most cases, is small compared to the ultrasonic carrier wavelength (1.5 mm for a 1-MHz ultrasonic carrier in water). As indicated in the schematic of FIG. 1, demodulator 113 is used to frequency down-shift the phase modulated carrier signal to baseband. Demodulators can be grouped into two categories depending on whether the demodulator recovers the phase or the frequency of the target surface. For the most common case in which the Doppler term dominates the modulation signal, a phase modulator will provide an output signal proportional to the surface displacement and a frequency demodulator will provide an output signal proportional to the surface velocity. FIGS. 2 and 3 depict two phase demodulation configurations.

For the phase demodulation configuration depicted in FIG. 2, the return signal from the transducer is divided by a power divider 201. For one part of the return signal, a narrow band filter 202 at frequency $f_C$ selects only the carrier frequency and the nearby frequencies included in the bandwidth of narrow band filter 202, while rejecting the modulation sidebands. A 90° phase shifter 203 then electronically sets the demodulator in quadrature (the most sensitive working point of the demodulator). The 90° phase shifter 203 may also be placed before narrow band filter 202. The divided return signals are then recombined in a mixer 204 and the resulting signal is filtered via a low pass filter 205 to remove the higher frequency signal (at twice the carrier frequency). The low frequency noise leading to a small frequency shift inside the bandwidth of narrow band filter 202 is not present in the demodulated output signal.

The phase demodulation scheme of FIG. 3 is based on a phase locked loop employing a low-pass filter 301 to feed back the signal variation associated with path instability to a mixer 304 via an amplifier 302 and a voltage controlled oscillator 303. The portion of the signal at frequencies below the cutoff frequency of low-pass filter 301 is considered to be noise, which is suppressed. A low-pass filter 305 filters out the higher frequencies from the mixed signal.

Figure 4:
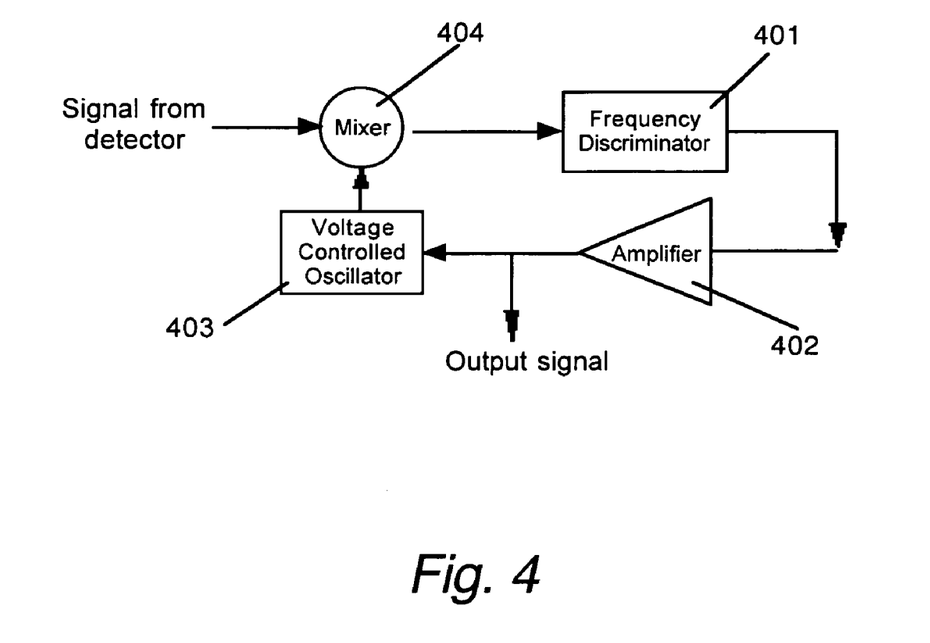
FIG. 4 is a block diagram of a frequency demodulator utilizing a discriminator.

FIG. 4 illustrates a frequency demodulator similar in principle to the phase demodulator of FIG. 3. In this case, low-pass filter 301 in the feedback loop of FIG. 3 is replaced with a frequency discriminator 401 in a feedback loop that includes an amplifier 402, a voltage controlled oscillator 403 and a mixer 404. When the Doppler contribution to the modulated signal is dominant, this frequency demodulator gives an output signal proportional to the surface velocity of the vibrating target, ensuring improved immunity to noise vibrations occurring at very low frequency. For the frequency demodulator of FIG. 4, the spectral noise power density increases with increasing frequency. This is not the case for the coherent phase demodulator of FIG. 2, which generally exhibits the lowest noise.

DESCRIPTION OF A PREFERRED EMBODIMENT

Figure 5:
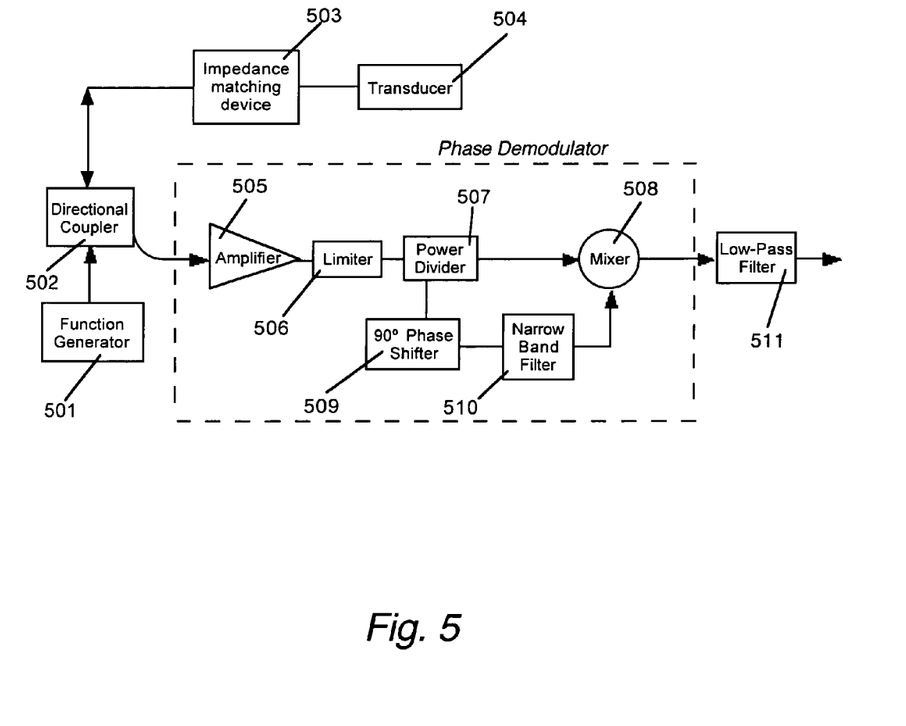
FIG. 5 is a block diagram of an electronic system for the probe of FIG. 1, according to the demodulation principles of FIG. 2.

FIG. 5 depicts a preferred electronic demodulation system. This system, which is based on the phase detection scheme of FIG. 2, was utilized for our experiments. A function generator 501 was used to generate a 1-MHz carrier signal. The output signal from the function generator was directed to a directional coupler 502 allowing transmission of the carrier signal to a transducer 504 in the fluid probe chamber, while separating the return modulated signal for later phase demodulation. An impedance matching device 503 was used to match the impedance of transducer 504 to the source impedance so as to minimize unwanted reflections. In this preferred embodiment, the same transducer is used for carrier generation and for detection of the modulated return signal beam so that directional coupler 502 is required. Transducer 504 is preferably designed to focus the generated ultrasonic beam to a small spot that couples effectively into the fluid stream. Alternatively, two transducers, mounted coaxially or adjacent to each other, may be used. The advantage in this case is that directional coupler 502 is not required. This eliminates any possibility of electrical feedback from the generated carrier to the demodulation circuit. However, the dual-transducer approach has its own risk of mechanical or electrical feedback from the generating unit to the detecting unit.

The phase demodulator of FIG. 5 converts the small phase change of the ultrasonic return signal to an electronic output signal that is proportional to the surface displacement when the Doppler effect is dominant. The return signal is first amplified by an amplifier 505 and is then passed through a limiter 506, which removes any amplitude modulation of the carrier. A power divider 507 then divides the return electrical signal into two parts. One part of the return signal passes through a 90° phase shifter 509 (to allow quadrature detection) and a narrow band filter 510, which selects only the carrier and rejects the frequency-shifted phase-modulated sidebands. The selected carrier is then mixed with the other split part of the return signal in mixer 508. Narrow band filter 510 is preferably based on a quartz crystal oscillator.

The bandwidth of narrow band filter 510 of FIG. 5 defines the bandwidth of the compensation. The 6-dB band pass of the narrow band quartz filter used for our experiments was 10 Hz, measured around the central frequency of 999.829 kHz. In this case, the demodulator has a reduced sensitivity below 10 Hz. For a phase demodulator, reduced sensitivity at low frequency is required to reject low frequency and large amplitude perturbations, and thus to maintain the detector in quadrature. The detected displacement amplitude should be small compared to the ultrasonic carrier wavelength, which is equal to 1.5 mm for 1-MHz ultrasonic waves propagated in water. For higher amplitude displacements, other demodulator schemes may be preferred.

Displacements on the order of a quarter of the ultrasonic wavelength will bring the demodulator out of quadrature. Large amplitude displacements usually occur at low frequency. The compensation bandwidth, determined by the crystal filter, must be large enough to include the possible low frequency, large amplitude vibrations due to noise. In the demodulator of FIG. 5, the compensation bandwidth is not adjustable. Nonetheless, the compensation bandwidth of 10 Hz was found to be sufficient to maintain the demodulator in quadrature during vibration monitoring experiments on a low-speed milling machine.

For the phase demodulator of FIG. 5, the signal exiting mixer 508 passes to a low-pass filter 511, which removes signal components at two times the carrier frequency. The cut-off frequency of low-pass filter 511 determines the upper frequency limit of the demodulator, which was arbitrarily chosen to be 10 kHz. The upper frequency limit of the demodulator is determined by the roll-off frequency of low pass filter 511 and, in principle, could be up to half of the carrier frequency (500 kHz in our experiments with a 1-MHz carrier). For the phase demodulator of FIG. 5, a stable carrier frequency is required. The frequency drift of the carrier must be less than the bandwidth of the quartz filter. For our experiments, we used an off-the-shelf function generator for which the output frequency at 1 MHz was stable within 1 Hz, which provided acceptable results.

For some applications, it is desirable to have an absolute calibration of the surface vibration amplitude. Calibration can be achieved, for example, by inserting a phase or frequency modulator between limiter 506 and power divider 507 of FIG. 5, or between power divider 507 and mixer 508. In this case, the modulator itself is separately calibrated to produce a known phase or frequency excursion for a given drive voltage. This known phase or frequency excursion is equivalent to a known surface vibration amplitude. In operation, the workpiece is strictly passive, with no induced vibrations. With the modulator operating at a predetermined frequency with a known phase or frequency excursion, a voltage is measured corresponding to the signal detected at the predetermined frequency. Thus, the response in volts per tool vibration unit (μm displacement or m/s velocity) can be determined. The modulator is then turned off and the tool vibration amplitude is measured using the measured voltage and the known response.

An important design requirement for the ultrasonic fluid probe of FIG. 1 is laminar fluid flow, which is needed so that turbulence within chamber 103 or fluid stream 109 does not distort the ultrasonic beam wavefront. Turbulence-induced wavefront distortion can reduce the amplitude of the transmitted beam and also cause backscattering that may appear as noise on the detected signal. Laminar flow may be attained by using a fluid of suitable viscosity, by using a baffle 107 (preferably between inlet 106 and the active end of transducer 102), by using a mildly tapered chamber, and by careful attention to the design of chamber outlet 108 to avoid protrusions in the fluid stream. It is also important that the fluid flow be stable. Preferably, the fluid is water-based and may be a cutting fluid, which typically has a viscosity between 1 and 18 centipoises. Chamber inlet 106 preferably has a cross-sectional area that is at least 5 times that of chamber outlet 108.

Figure 6:
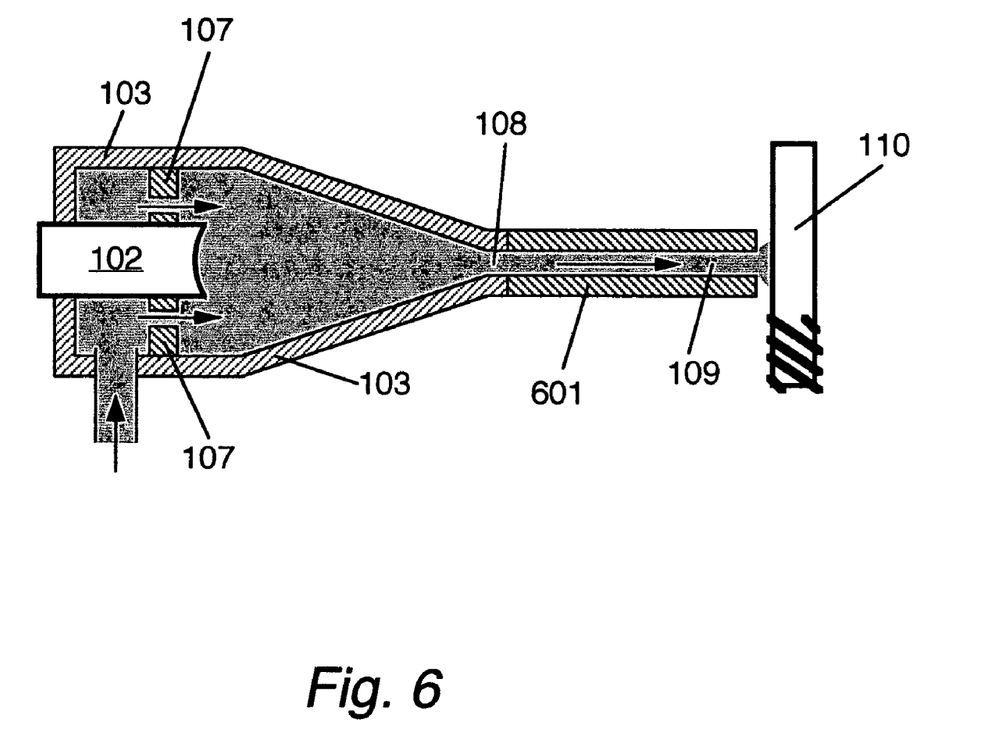
FIG. 6 illustrates an ultrasonic fluid probe utilizing a waveguide comprising a fluid stream confined in a rigid tube in accordance with the present invention.
Figure 7:
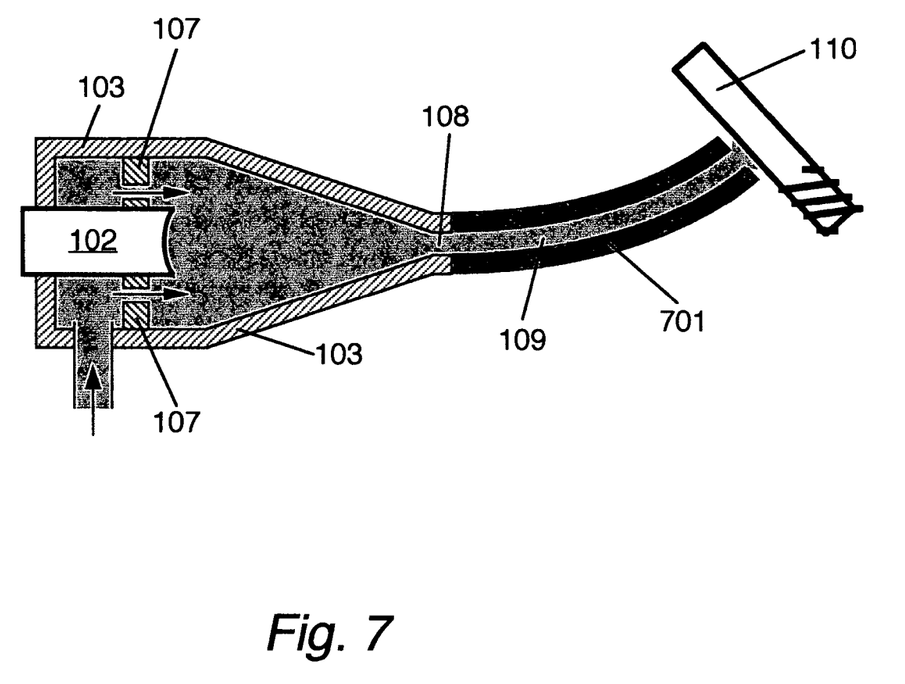
FIG. 7 illustrates an ultrasonic fluid probe utilizing a waveguide comprising a fluid stream confined in a flexible tube in accordance with the present invention.
Figure 8:
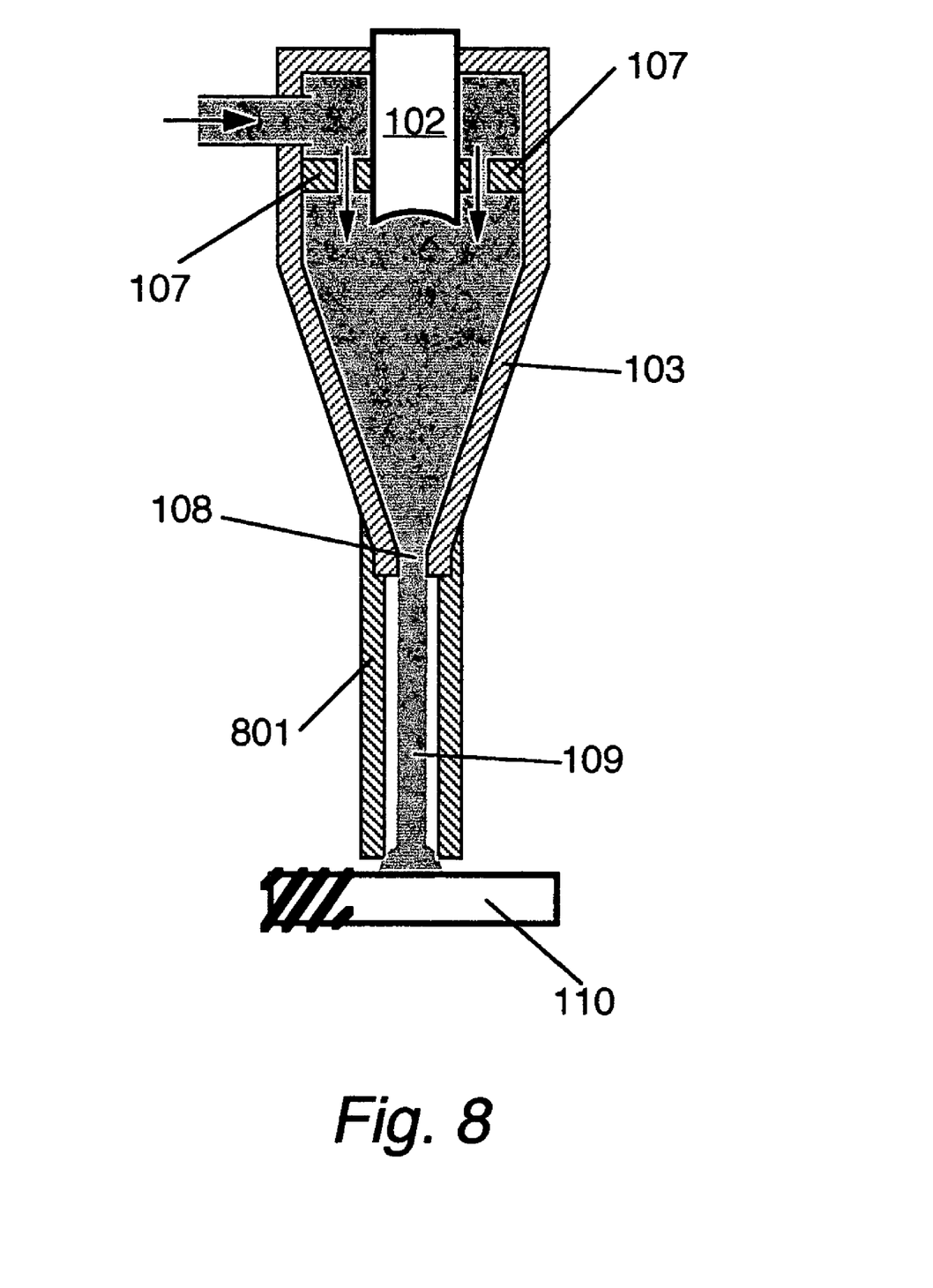
FIG. 8 illustrates an ultrasonic fluid probe utilizing a waveguide comprising a free-standing fluid stream with a protective rigid tube in accordance with the present invention.

FIGS. 6, 7 and 8 show alternative embodiments of the ultrasonic probe of FIG. 1 employing, respectively, a straight confinement tube 601 (FIG. 6), a flexible confinement tube 701 (FIG. 7), and a protective tube 801 (FIG. 8) for the fluid stream. Common reference numbers in FIGS. 6–8 represent identical or substantially similar components as described in connection with the fluid probe illustrated in FIG. 1. Typically, one end of tube 601, 701 or 801 is attached to chamber 103 around outlet 108 and the other end of the tube is spaced apart from target 110 to leave a small gap through which the fluid in the fluid stream can escape. Fluid fills confinement tubes 601 and 701 so that the fluid and the surrounding tube form a composite waveguide that is effective for distances up to at least 8 inches. A confinement tube enables use of low fluid flow rates to avoid fluid turbulence. Flexible confinement tube 701 may enable vibration monitoring of areas of target 110 that would be otherwise inaccessible. Protective tube 801 protects free-standing fluid stream 109 from disruption by machining debris and cutting fluid spray. Protective tube 801 is especially suitable for a substantially vertical fluid stream.

Vibration Measurements

The efficacy of the present invention was demonstrated via ultrasonic vibration measurements on static tools and on tools during machining at low speed. Measurements were made using the ultrasonic probe system depicted in FIG. 1 and the demodulation system depicted in FIGS. 2 and 5. Outlet 108 had a diameter of about 3/16 inches. The output of transducer 102 was a 1-MHz ultrasonic beam that was focused on chamber outlet 108. Special care was taken to ensure that back reflection from the chamber walls was minimal. A baffle plate 107 was used to prevent turbulence and provide laminar flow. The fluid used was tap water.

Figure 9:
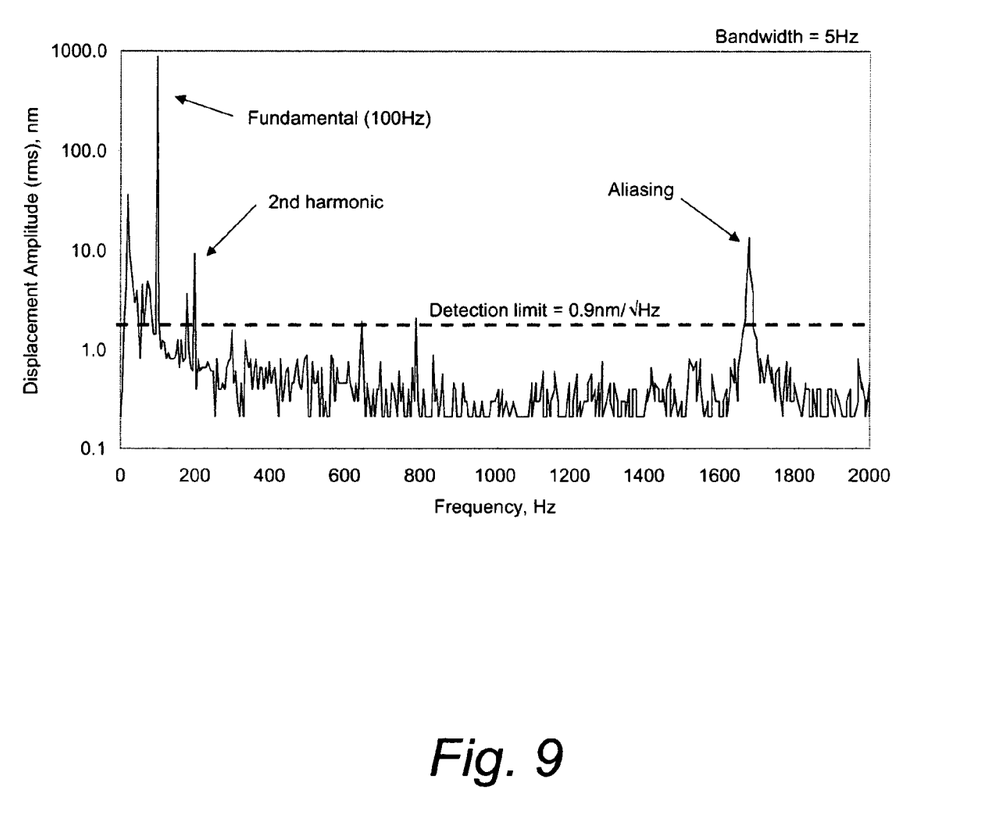
FIG. 9 is a plot of displacement amplitude vs. vibration frequency illustrating the sensitivity of the fluid probe of the present invention for detecting vibration of a target. The fluid probe was very close to the target and the fluid flow rate was very low.

FIG. 9 illustrates the displacement sensitivity for the fluid probe at a very low fluid flow rate at which fluid flow is laminar. For this experiment, the fluid probe was positioned very close to the target, which was a flat mirror attached to a shaker vibrating at 100 Hz with a 0.9 μm rms amplitude. The fundamental signal at 100 Hz and several harmonics are observed. An additional single frequency spike, attributable to signal aliasing, is clearly visible. The detection limit was determined from the noise floor to be 0.9 nm/(Hz)$^{1/2}$.

Figure 10:
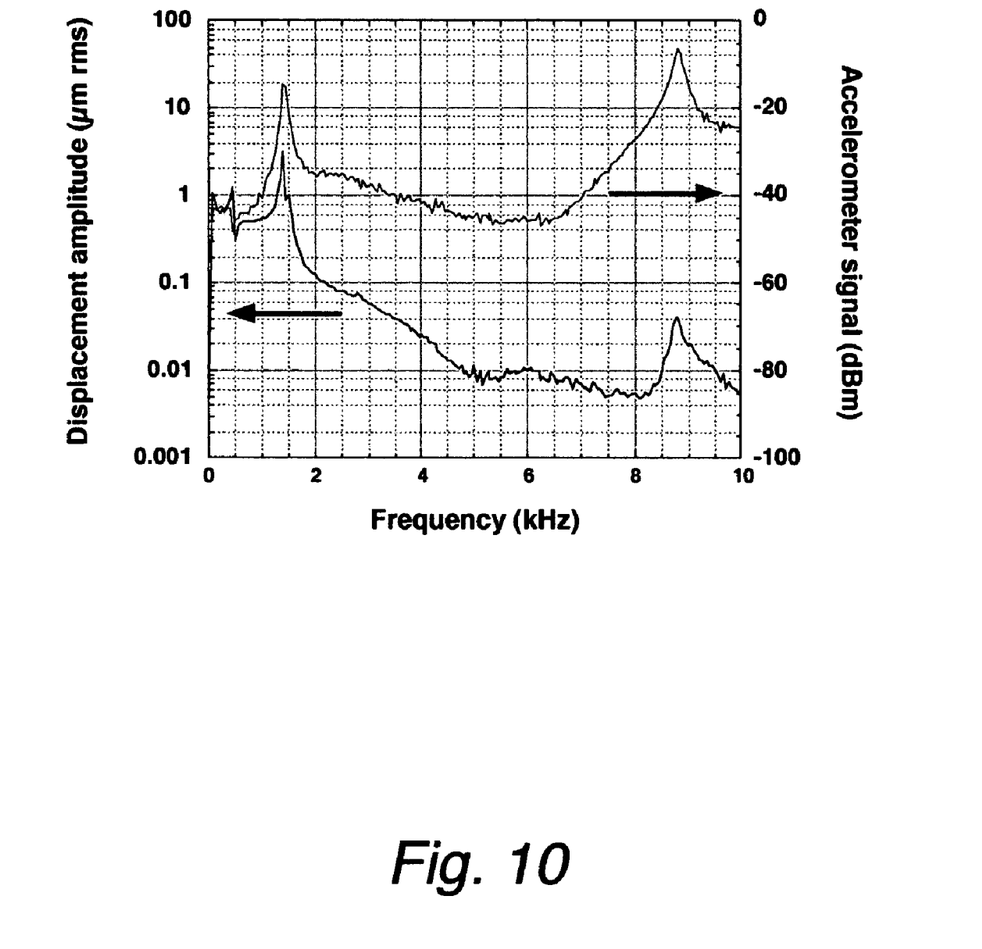
FIG. 10 shows a comparison of the frequency response of a ⅜-inch diameter, 2-inch long end mill measured by the fluid probe of the present invention and by an accelerometer attached to the end mill.

The fluid probe of FIG. 1 was also used to measure the dynamic response of a tool excited by an impact hammer. In this case, the frequency response of a 3/8-inch diameter, 2-inch long end mill was measured. The impact was produced by an impact hammer with an impact force measured at 60N. The fluid probe was located just above the flute, on the clear shaft. For comparison, an accelerometer was then mounted at the same location and the experiment was repeated. FIG. 10 shows a comparison between the frequency response recorded with the fluid probe and the accelerometer. Keeping in mind that the accelerometer signal increases with the frequency squared, there is an excellent agreement between the two frequency responses.

Figure 11:
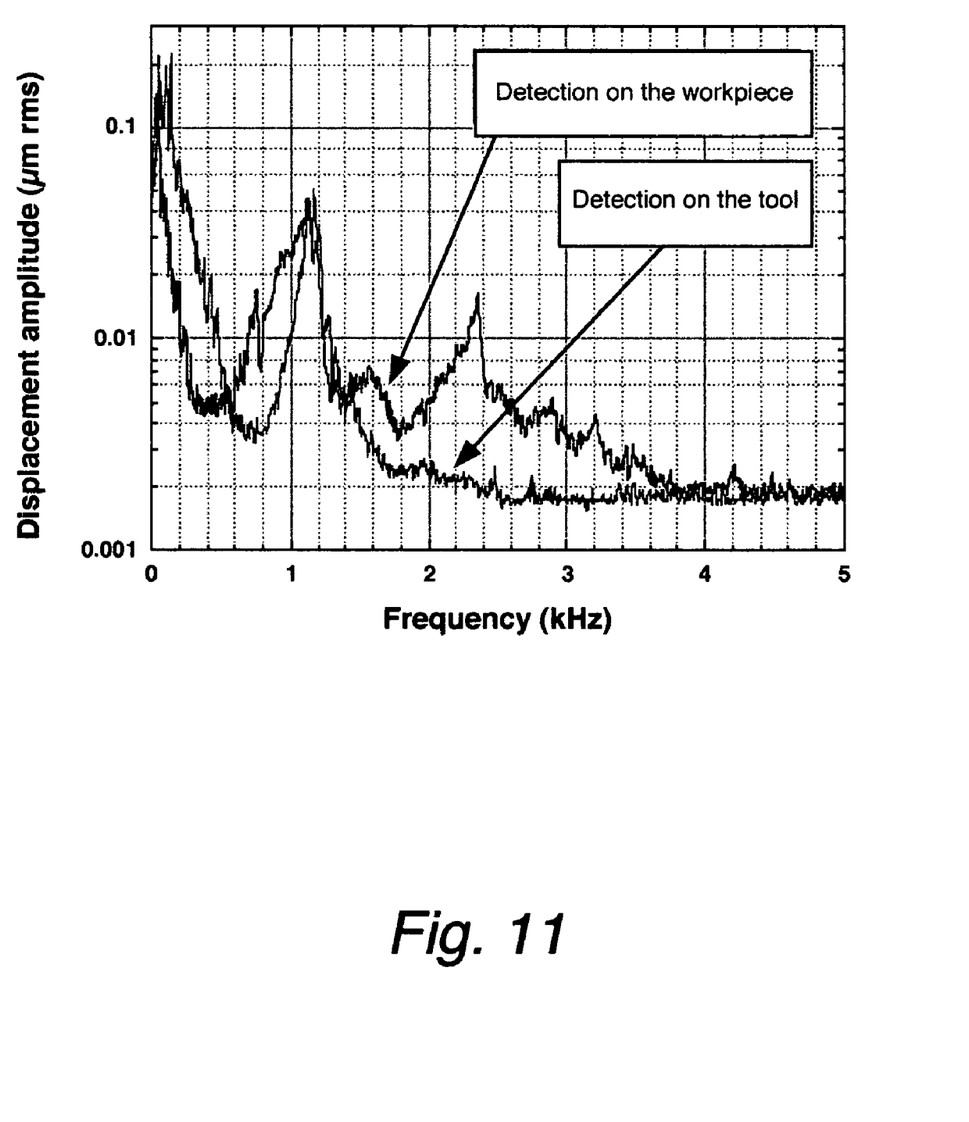
FIG. 11 shows ultrasonic vibrational displacement spectra for a cutting tool (rotating at 630 rpm) and a workpiece (1/16-inch thick steel plate) measured during a machining operation using the ultrasonic vibration probe of the present invention.

Tool vibration monitoring during low speed machining was also demonstrated using the active ultrasonic fluid probe of FIG. 1. FIG. 11 shows the vibration spectrum of a tool measured during cutting at 630 RPM. The fluid probe was located just above the flute on the clear shaft. The workpiece was a 1/16-inch thick steel plate (1×3 inches). The workpiece was fed at constant slow speed. FIG. 11 also shows the vibration spectrum of the workpiece, measured with the fluid probe during the cutting operation. This spectrum exhibits additional features detected only for the workpiece. Since the workpiece was more flexible than the tool, larger vibrational motion of the workpiece was expected. Such behavior is generally encountered with difficult-to-machine materials, for which vibration of the workpiece during machining can be a limiting factor. In such cases, vibration monitoring of the workpiece is also needed.

The preferred embodiments of this invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

We claim:

1. A method for ultrasonically detecting vibration of a target, comprising the steps of:
   causing a stream of a fluid to flow to the target from an outlet in a chamber containing the fluid;
   providing an ultrasonic carrier beam of a predetermined frequency in the fluid by means of a first transducer in contact with the fluid in the chamber, said carrier beam being propagated along the fluid stream to the target;
   converting a reflected ultrasonic beam to a return electrical signal by means of the first transducer or a second transducer in contact with the fluid in the chamber;
   demodulating the return electrical signal so as to provide a measure of a vibrational characteristic of the target;
   measuring a noise signal produced by vibration of at least one of said transducers; and
   canceling the noise signal from the return electrical signal.

2. The method of claim 1, wherein the target comprises a cutting tool or a workpiece.

3. The method of claim 1, wherein the ultrasonic carrier beam is a focused ultrasonic beam.

4. The method of claim 1, wherein the predetermined frequency is between 100 kHz and 10 MHz.

5. The method of claim 1, wherein the ultrasonic carrier beam is a continuous ultrasonic beam.

6. The method of claim 1, wherein the vibrational characteristic is selected from the group consisting of surface displacement and surface velocity.

7. The method of claim 1, further comprising the step of:
   introducing an electrical time delay into the signal path via analog electronic means or via a separate ultrasonic delay line,
   whereby a signal enhancement is provided.

8. The method of claim 1, further comprising the step of: calibrating the vibrational characteristic of the target by means of a phase modulator or a frequency modulator.

9. A device for ultrasonically detecting vibration of a target, comprising:
- a fluid;
- a chamber containing the fluid and having an outlet through which a stream of the fluid is caused to flow from the chamber to the target;
- a fluid source in fluid communication with said chamber;
- a means for causing the fluid to flow from said fluid source through said chamber to the target;
- a driver for providing an electrical signal of a predetermined frequency;
- a transducer in contact with the fluid in the chamber and driven by said driver to generate an ultrasonic carrier beam that is propagated along the stream of the fluid to the target, wherein said transducer also detects a reflected ultrasonic beam from the target and generates a return electrical signal;
- a directional coupler, disposed between said driver and said transducer;
- a contact accelerometer for detecting vibration of said transducer; and
- a demodulator for processing the return electrical signal so as to provide a measure of a vibrational characteristic of the target.

10. The device of claim 9, further comprising a baffle within said chamber for providing laminar flow of the fluid.

11. The device of claim 9, further comprising a confinement tube for the stream of the fluid.

12. The device of claim 9, further comprising a protective tube for the stream of the fluid.

13. A device for ultrasonically detecting vibration of a target, comprising:
- a fluid;
- a chamber containing the fluid and having an outlet through which a stream of the fluid is caused to flow from the chamber to the target;
- a fluid source in fluid communication with said chamber;
- a means for causing the fluid to flow from said fluid source through said chamber to the target;
- a driver for providing an electrical signal of a predetermined frequency;
- a transducer in contact with the fluid in the chamber and driven by said driver to generate an ultrasonic carrier beam that is propagated along the stream of the fluid to the target, wherein said transducer also detects a reflected ultrasonic beam from the target and generates a return electrical signal;
- a directional coupler, disposed between said driver and said transducer;
- a demodulator for processing the return electrical signal so as to provide a measure of a vibrational characteristic of the target; and
- a phase modulator or a frequency modulator for calibrating the demodulator.

14. A device for ultrasonically detecting vibration of a target, comprising:
- a fluid;
- a chamber containing the fluid and having an outlet through which a stream of the fluid is caused to flow from the chamber to the target;
- a fluid source in fluid communication with said chamber;
- a means for causing the fluid to flow from said fluid source through said chamber to the target;
- a driver for providing an electrical signal of a predetermined frequency;
- a first transducer in contact with the fluid in the chamber and driven by said driver to generate an ultrasonic carrier beam that is propagated along the stream of the fluid to the target;
- a second transducer that detects a reflected ultrasonic beam from the target and generates a return electrical signal;
- a demodulator for processing the return electrical signal so as to provide a measure of a vibrational characteristic of the target; and
- a contact accelerometer for detecting vibration of said transducer.

15. The device of claim 14, further comprising a baffle within said chamber for providing laminar flow of the fluid.

16. The device of claim 14, further comprising a confinement tube for the stream of the fluid.

17. The device of claim 14, further comprising a protective tube for the stream of the fluid.

18. A device for ultrasonically detecting vibration of a target, comprising:
- a fluid;
- a chamber containing the fluid and having an outlet through which a stream of the fluid is caused to flow from the chamber to the target;
- a fluid source in fluid communication with said chamber;
- a means for causing the fluid to flow from said fluid source through said chamber to the target;
- a driver for providing an electrical signal of a predetermined frequency;
- a first transducer in contact with the fluid in the chamber and driven by said driver to generate an ultrasonic carrier beam that is propagated along the stream of the fluid to the target;
- a second transducer that detects a reflected ultrasonic beam from the target and generates a return electrical signal;
- a demodulator for processing the return electrical signal so as to provide a measure of a vibrational characteristic of the target; and
- a phase modulator or a frequency modulator for calibrating the demodulator.

* * * * *